United States Patent [19]

Touzan et al.

[11] Patent Number: 5,468,496
[45] Date of Patent: Nov. 21, 1995

[54] TWO-PHASE COSMETIC OR DERMATOLOGICAL COMPOSITION

[75] Inventors: Philippe Touzan, Ramonville-Saint-Agne; Liliane Lukassen, Chevilly-Larue; Nathalie Louvet, L'Hay-Les-Roses, all of France

[73] Assignee: L'Oreal, Paris, France

[21] Appl. No.: 165,997

[22] Filed: Dec. 14, 1993

[30] Foreign Application Priority Data

Dec. 18, 1992 [FR] France .................................. 92 15309

[51] Int. Cl.$^6$ ...................................................... A61K 7/02
[52] U.S. Cl. .......................... 424/401; 252/358; 514/846; 514/937
[58] Field of Search ........................... 424/401; 514/938, 514/937, 785, 789, 846; 252/319, 320, 344, 358

[56] References Cited

U.S. PATENT DOCUMENTS

| | | | |
|---|---|---|---|
| 3,819,589 | 6/1974 | Fauke et al. | 525/327.6 |
| 3,928,194 | 12/1975 | Tao | 252/328 |
| 4,278,657 | 7/1981 | Tezuka et al. | 424/63 |
| 4,374,734 | 2/1983 | Newcombe | 210/708 |
| 4,609,488 | 9/1986 | Geke et al. | 252/344 |
| 4,659,573 | 4/1987 | Frischling et al. | 424/63 |
| 4,806,572 | 2/1989 | Kellett | 521/112 |
| 4,919,846 | 4/1990 | Nakama et al. | 252/542 |
| 5,165,917 | 11/1992 | Zabotto et al. | 424/401 |
| 5,217,641 | 6/1993 | Herstein | 252/171 |
| 5,308,401 | 5/1994 | Geke et al. | 134/2 |

FOREIGN PATENT DOCUMENTS

| | | |
|---|---|---|
| 0046594 | 3/1982 | European Pat. Off. |
| 2638636 | 11/1990 | France . |
| 53-080460 | 7/1978 | Japan . |
| 54-024908 | 2/1979 | Japan . |
| 61-129033 | 6/1986 | Japan . |
| 62-059204 | 8/1987 | Japan . |
| 2071495 | 9/1981 | United Kingdom . |
| 2219937 | 12/1989 | United Kingdom . |
| 90/10429 | 9/1990 | WIPO . |

Primary Examiner—Melvyn I. Marquis
Assistant Examiner—Robert H. Harrison
Attorney, Agent, or Firm—Oliff & Berridge

[57] ABSTRACT

A cosmetic or dermatological composition has an aqueous phase and a separate oily phase in a ratio of between 30:70 and 60:40, at least one of the phases containing a surfactant, the aqueous phase containing a demixing agent in a proportion of between 0.025% and 5% by weight, the demixing agent having the formula:

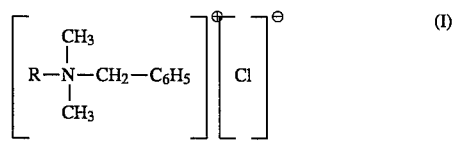

in which:

R represents a saturated linear alkyl radical having from 12 to 16 carbon atoms. The composition may be used for any cosmetic or dermatological purpose, particularly for removing makeup from the eyes or face, as a sun lotion or as a lotion for cleansing or care of the skin.

8 Claims, No Drawings

TWO-PHASE COSMETIC OR DERMATOLOGICAL COMPOSITION

The present invention relates to a cosmetic or dermatological composition for makeup removal or cleansing or care of the skin, consisting of two separate phases, an aqueous phase and an oily phase, which emulsifies readily on shaking but whose constituents segregate rapidly on standing.

Compositions of this type, consisting of two separate phases, in particular an aqueous phase and an oily phase, are generally designated by the term "two-phase composition". The use of the said compositions necessitates a prior shaking in order to form an emulsion, the latter having to be of sufficient quality and stability to permit a homogeneous application of the two phases. On standing, the said phases should separate rapidly and regain their initial state, this phenomenon being better known by the term "demixing".

Two-phase compositions have already been described in Patent FR 88/14,641 (2,638,636), in particular for removing makeup from the eyes. The compositions of this patent, while having excellent makeup removal properties, present problems of demixing inasmuch as, after shaking, they tend to remain in the emulsified state.

With each successive shaking, this phenomenon becomes accentuated, and the demixing times can then reach several hours or even several days.

Furthermore, this phenomenon is enhanced by the presence of large amounts of heavy oils and/or of surfactants in the composition, which involves reducing the amount of surfactant and preferring light and volatile oils rather than heavy oils.

Now, obtaining rapid demixing is desirable for various reasons, in particular because a poor separation of the two phases is perceived by users as being unattractive.

In addition, in this type of two-phase composition, it is generally useful to be able to incorporate fat-soluble active principles in the oily phase, but these latter are, for the most part, unstable in contact with a hydrophilic phase. Among these lipophilic active principles which are unstable in contact with a hydrophilic phase, there may be mentioned, in particular, dermatological active principles, for instance antifungal agents such as econazole and miconazole, antibacterial agents such as chlorguinol, hexachlorophene and usnic acid, keratolytic derivatives such as salicylic acid and anti-inflammatories such as α-oryzanol and α-bisabolol. In order to maintain the integrity of these active principles, it is hence especially desirable to limit their time of contact with the hydrophilic phase, and consequently to speed up the demixing process.

After a large number of studies, it has now been found, surprisingly and unexpectedly, that, by combining a surfactant and a particular demixing agent, compositions which emulsify readily on shaking and whose constituents segregate rapidly on standing are obtained.

The subject of the present invention is a nonfoaming cosmetic or dermatological composition presented in two-phase form, consisting of an aqueous phase and a separate oily phase in a ratio of between 30:70 and 60:40, at least one of the said phases containing a surfactant, characterized in that it contains, in addition, in the said aqueous phase, a demixing agent in a proportion of between 0.025% and 5% by weight, the said agent being an alkyldimethylbenzylammonium chloride of formula:

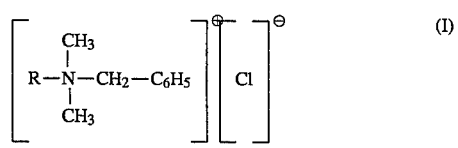

in which:

R represents a saturated linear alkyl radical essentially having from 12 to 16 carbon atoms, or a mixture of alkyldimethylbenzylammonium chlorides of formula (I), and in that the said surfactant is present in a proportion of greater than 0.25% by weight relative to the weight of the composition, the surfactant being of the anionic, nonionic or amphoteric type when it is present in the aqueous phase or of the fat-soluble nonionic type when it is present in the oily phase.

Preferably, the demixing agent used in the composition according to the invention is a mixture of alkyldimethylbenzylammonium chlorides of formula (I), consisting of approximately 65% by weight of lauryldimethylbenzylammonium chloride, approximately 23% by weight of myristyldimethylbenzylammonium chloride and approximately 8% by weight of palmityldimethylbenzylammonium chloride, the remainder consisting of at least one alkyldimethylammonium chloride in which the radical has fewer than 12 or more than 16 carbon atoms.

As a mixture of alkyldimethylbenzylammonium chlorides which can be used according to the invention, there may be mentioned that marketed under the name "benzalkoniumchloride" by the company Fluka, the characteristics of which are as follows:

Molecular weight: 360

Melting point: 35° C.

For the purpose of demonstrating the excellent demixing properties of the alkyldimethylbenzylammonium chlorides used according to the invention, a large number of tests were performed on different quaternary ammonium compounds of structure related to that of the compounds of formula (I).

Thus, studies performed with the following compounds: oleyldimethylbenzylammonium chloride, distearyldimethylammonium chloride, stearyldimethylbenzylammonium chloride, myristyltrimethylammonium bromide, lauryltrimethylammonium chloride, lauryltrimethylanunoniumbromide, stearyltrimethylammoniumbromide, myristalkonium chloride and cethexonium bromide, proved to show that none of these had any influence on demixing. Altogether surprisingly, only the alkyldimethylbenzylammonium chlorides of formula (I) and mixtures thereof proved to display this property of a demixing agent. This is all the more surprising for the fact that these compounds are amphiphilic molecules which are known, furthermore, to be surfactants, and that consequently they should stabilize the mixture of aqueous and oily phases instead of promoting their separation.

Among anionic surfactants which may be present in the aqueous phase of the composition according to the invention, there may be mentioned, in particular:

the alkyl ether sulphates such as the product sold under the name "Texapon ASV" by the company Henkel, alkyl sulphoacetates such as the product sold under the name "Lathanol Lal" by the company Stepan, alkyl sulphosuccinates such as the product sold under the name "sodium dioctyl sulphosuccinate" by the company Rhone Poulenc, alkylamido sulphosuccinates such as the product sold under the name "Rewoderm S 1333" by the company Rewo, alkylamido polypeptides such as the product sold under the name "Lamepon S" by the company Grunau, and alkylsarcosinates such as the product sold under the name "Oramix L 30" by the company Seppic.

Among amphoteric surfactants which may be present in the aqueous phase of the composition according to the invention, there may be mentioned, in particular:

alykylamidopropyldimethylbetaines such as the product sold under the name "Tego Betaine L 7" by the company Goldschmidt, alkylamidobetaines such as the product sold under the name "Incronam 30" by the company Croda, imidazoline derivatives such as the product sold under the name "Chimexane HD" by the company Chimex, and Sodium salt of N-(N'-acylaminoethyl)N-hydroxyethyl β-alanine, such as the product sold under the name "Monateric Isa 35" by the company Mona.

According to a preferred embodiment of the invention, the surfactant present in the aqueous phase of the two-phase composition is of the nonionic type.

Among nonionic surfactants, those which are especially preferred are:

polyoxyethylenated sorbitol esters such as the product sold under the name "Tween 20" by the comply Atlas, polyoxyethylenated fatty alcohols such as the product sold under the name "Remcopal 21912 AL" by the company Gerland, polyoxyethylenated alkylphenols such as the product sold under the name "Triton X 100" by the company Rohm-Haas, condensates of ethylene oxide and propylene oxide such as those sold under the names "Synperonic PE" by the company ICI, and especially those designated by the references L31, L64, P38, P88, L92, P103, F108 and F127, and polyoxyethylene, polyoxypropylene block polymers such as those sold under the name "Poloxamer" or "Pluronic" by the company BASF.

Among fat-soluble nonionic surfactants which may be present in the oily phase of the composition according to the invention, there may be mentioned, in particular:

esters of a fatty acid having 12 to 18 carbon atoms and sorbitol, such as polysorbate 85 sold under the name "Tween 85" by the company ICI or the "Arlacel" range also sold by the company ICI, polyglycerolated fatty acid esters having 12 to 18 carbon atoms, such as the polyglycerolated dioleate sold under the name "Decaglyn 2-0" by the company Nikkol, oxyethylenated fatty alcohols and oxyethylenated alkylphenols, such as nonoxynol 7 which is an oxyethylenated nonylphenol containing 7 mol of EO, sold under the name "Synperonic NP7" by the company ICI.

According to a pre#erred embodiment of the invention, the proportion of surfactant present in at least one of the said phases is between 0.5% and 10% by weight relative to the total weight of the composition.

The ratio of the surfactant to the demixing agent is preferably between 0.1:1 and 200:1.

The aqueous phase of the composition can consist of sterile demineralized water or of a flower water such as rose water, cornflower water, chamomile water or limeblossom water.

The oily phase of the two-phase composition according to the invention consists of a mixture of oils, it being possible for the latter to be mineral, vegetable or synthetic oils or alternatively silicone oils.

Among mineral oils which can constitute the oily phase, there may be mentioned, in particular, liquid paraffin and higher aliphatic hydrocarbons such as, for example, isohexadecane; among vegetable oils, jojoba oil as well as safflower oil; among silicone oils, cyclopentadimethylsiloxane sold under the name "Volatile Silicone 7158" by the company Union Carbide, and among synthetic products, alkylpalmitates in which the alkyl radical has from 2 to 10 carbon atoms, such as isopropyl palmitate or 2-ethylhexyl palmitate, and alkyl adipates in which the alkyl radical has from 2 to 10 carbon atoms, such as bis(2-ethylhexyl) adipate.

According to a preferred embodiment of the invention, the oily phase consists of at least one oil chosen from a cyclomethicone in a proportion of from 1 to 80%, isohexadecane from 1 to 50%, octylpalmitate from 1 to 50% and dioctyl adipate from i to 50% by weight relative to the total weight of the oily phase.

The two-phase composition according to the invention can also contain conventional cosmetic or dermatological adjuvants present in at least one of the two phases, depending on their hydrophilic or lipophilic nature, such as, for example, perfumes, preservatives, colorants, emollients, a buffer, humectants and, where appropriate, an electrolyte such as sodium chloride to make the aqueous phase isotonic.

Among humectants, there may be mentioned, in particular, glycerol and glycols such as hexylene glycol, polyethylene glycol 600 and polypropylene glycol, these being present at a concentration of between 0.05 and 2%.

Among emollients, special mention may be made of allantoin and certain plant extracts.

The two-phase composition according to the invention may be used for any cosmetic or dermatological purpose, and in particular for removing makeup from the eyes or face, as a sun lotion or as a lotion for cleansing or care of the skin.

Several examples of cosmetic compositions for makeup removal or cleansing and care of the skin according to the invention will now be given by way of illustration.

EXAMPLE 1

A two-phase makeup removal lotion for the eyes, according to the invention, is obtained by packaging in a bottle 48% of an oily phase (A) and 52% of an aqueous phase (B) containing the following ingredients:

|  | % |
| --- | --- |
| A - Oily phase |  |
| Octyl palmitate | 30 |
| Dioctyl adipate | 15 |
| Cyclomethicone | 55 |
| B - Aqueous phase |  |
| Polyoxyethylene, polyoxypropylene block polymer sold by the company BASF under the name "Poloxamer 407" | 0.5 |
| Dipotassium phosphate | 0.3 |
| Monopotassium phosphate | 0.1 |
| Sodium chloride | 0.9 |
| Mixture of alkylmethylbenzylammonium chlorides marketed under the name "benzalkonium chloride" by the company Fluka | 0.1 |
| Perfume | 0.0175 |
| Preservatives qs |  |

-continued

| | % |
|---|---|
| Water | qs 100 |

After shaking and use, complete demixing between the two phases takes place after approximately 15 minutes at room temperature.

EXAMPLE 2

A two-phase emollient and hydrating lotion for the body, according to the invention, is obtained by packaging in a bottle 50% of an oily phase (A) and 50% of an aqueous phase (B) containing the following ingredients:

| | % |
|---|---|
| A - Oily Phase | |
| Cyclomethicone | 30 |
| Isohexadecane | 20 |
| Liquid paraffin | 47 |
| Jojoba oil | 3 |
| B - Aqueous phase | |
| Mixture of alkylmethylbenzylammonium chlorides marketed under the name "benzalkonium chloride" by the company Fluka | 0.15 |
| Polysorbate 20 sold by the company ICI under the nine "Tween 20" | 2 |
| Glycerol | 6 |
| Preservatives qs | |
| Water | qs 100 |

EXAMPLE 3

A two-phase sun lotion according to the invention is obtained by packaging in a bottle 7.0% of an oily phase (A) and 30% of an aqueous phase (B) containing the following ingredients:

| | % |
|---|---|
| A - Oily phase | |
| Octyl palmitate | 20 |
| Isohexadecane | 50 |
| Dioctyl adipate | 25 |
| 2-Ethylhexyl p-methoxycinnamate | 5 |
| B - Aqueous phase | |
| Mixture of alkylmethylbenzylammonium chlorides marketed under the name "benzalkonium chloride" by the company Fluka | 0.20 |
| Polyoxyethylene, polyoxypropylene block polymer sold by the company BASF under the name "Poloxamer 184" | 1 |
| Polypropylene glycol | 3 |
| Preservatives qs | |
| Water | qs 100 |

EXAMPLE 4

A two-phase emollient and makeup removal lotion for the face, according to the invention, is obtained by packaging in a bottle 45% of an oily phase (A) and 55% of an aqueous phase (B) containing the following ingredients:

| | % |
|---|---|
| A - Oily phase | |
| Isohexadecane | 39 |
| Cyclomethicone | 60 |
| Sorbitan laurate sold by the company ICI under the name "Arlacel 20" | 1 |
| B - Aqueous Phase | |
| Monopotassium phosphate | 0.1 |
| Dipotassium phosphate | 0.3 |
| Mixture of alkylmethylbenzylammonium chlorides marketed under the name "benzalkonium chloride" by the company Fluka | 0.04 |
| Rose water | 20 |
| Colorant | 0.05 |
| EDTA tetrasodium salt | 0.1 |
| Preservatives qs | |
| Water | qs 100 |

What is claimed is:

1. A cosmetic or dermatological composition comprising an aqueous phase and a separate oily phase in a ratio of between 30:70 and 60:40, at least one of the said phases containing an anionic, nonionic or amphoteric surfactant, said aqueous phase containing a demixing agent in a proportion of between 0.025% and 5% by weight, said demixing agent having the formula:

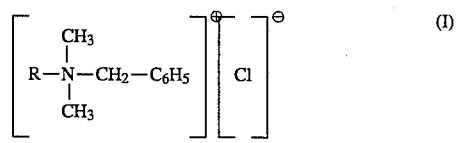

in which:

R represents a saturated linear alkyl radical having from 12 to 16 carbon atoms, or a mixture of compounds of formula (I), and said anionic, nonionic or amphoteric surfactant being present in a proportion of more than 0.25% by weight relative to the weight of the composition and being selected from the group consisting of anionic, nonionic and amphoteric surfactant when being present in the aqueous phase or said anionic, nonionic or amphoteric surfactant being a fat-soluble nonionic surfactant when being present in the oily phase, wherein said composition is nonfoaming.

2. The composition according to claim 1, wherein said demixing agent is a mixture consisting essentially of 65% by weight of lauryldimethylbenzylammonium chloride, 23% by weight of myristyldimethylbenzylammonium chloride and 8% by weight of palmityldimethylbenzylammonium chloride, the remainder being at least one alkyldimethylammonium chloride in which the alkyl radical has less than 12 or more than 16 carbon atoms.

3. The composition according to claim 1, wherein the anionic, nonionic or amphoteric surfactant is present in a proportion of between 0.5 and 10% by weight relative to the total weight of the composition.

4. The composition according to claim 1, wherein the ratio of the anionic, nonionic or amphoteric surfactant to the demixing agent is between 0.1:1 and 200:1.

5. The composition according to claim 1, wherein the oily phase contains at least one oil selected from the group consisting of liquid paraffin, isohexadecane, silicone oil, alkyl palmitate or alkyl adipate wherein the alkyl radical has 2 to 10 carbon atoms, jojoba oil and safflower oil.

6. The composition according to claim 1, wherein the oily phase contains at least one oil selected from the group consisting of cyclomethicone in a proportion of 1 to 80%, isohexadecane in a proportion of 1 to 50%, octylpalmitate in a proportion of 1 to 50% and dioctyl adipate in a proportion of 1 to 50% by weight relative to the total weight of the oily phase.

7. The composition according to claim 7, which further contains in at least one of the two phases, at least one conventional cosmetic adjuvant selected from the group consisting of a perfume, a preservative, a colorant, an emollient, a buffer, a humectant and an electrolyte.

8. The composition according to claim 1, wherein the composition is a two-phase lotion for skin care.

* * * * *